United States Patent [19]

Rule et al.

[11] Patent Number: 4,863,710

[45] Date of Patent: Sep. 5, 1989

[54] OXIDATION HYDROLYSIS OF IODOALKANES

[75] Inventors: Mark Rule; Victor H. Agreda, both of Kingsport, Tenn.

[73] Assignee: Eastman Kodak Company, Rochester, N.Y.

[21] Appl. No.: 220,844

[22] Filed: Jul. 15, 1988

[51] Int. Cl.$^4$ .................... C01B 7/14; C07C 29/09
[52] U.S. Cl. .................... 423/500; 568/891
[58] Field of Search .............. 568/891, 39, 62, 75; 260/687 H; 423/502, 500

[56] References Cited

U.S. PATENT DOCUMENTS

| | | | |
|---|---|---|---|
| 1,849,844 | 3/1932 | Lloyd et al. | 568/891 |
| 3,006,731 | 10/1961 | MaGovern et al. | 423/502 |
| 3,425,798 | 2/1969 | Statman et al. | 423/500 |
| 3,839,547 | 10/1974 | McNulty et al. | 423/502 |
| 3,975,439 | 8/1976 | Klalundi | 564/407 |
| 4,085,200 | 4/1978 | Schulten et al. | 423/579 |

FOREIGN PATENT DOCUMENTS

| | | |
|---|---|---|
| 0218998 | 4/1987 | European Pat. Off. |
| 73489 | 6/1978 | Japan. |
| 887678 | 1/1962 | United Kingdom ........ 568/891 |

*Primary Examiner*—John Doll
*Assistant Examiner*—Brian M. Bolam
*Attorney, Agent, or Firm*—Charles R. Martin; William P. Heath, Jr.

[57] ABSTRACT

A process comprising preparation of an alkanol and elemental iodine by contacting an iodoalkane containing 1 to 20 carbons, water and molecular oxygen at a temperature in the range of about 50° to about 200° C. and recovering the elemental iodine.

4 Claims, No Drawings

OXIDATION HYDROLYSIS OF IODOALKANES

This invention relates to the oxidation hydrolysis of iodoalkanes wherein an alkanol and elemental iodine are produced by contacting an iodoalkane, water and molecular oxygen. Since the iodine is in the elemental form, it can be easily recovered.

A number of processes have been developed to recover iodine values from inorganic iodide containing compounds. For example, iodine is commercially recovered from deep well brines by chlorine oxidation. Iodine values can also be recovered by oxidation of acidic brines with cupric sulfate or ferric sulfate. Alternatively, electrolysis of ammonium iodide solutions has been disclosed in U.S. Pat. No. 3,975,439. The catalytic oxidation of ammonium iodide solutions by oxygen in the presence of copper catalysts has been disclosed in Japanese Patent Application Kokai No. 73489/1978. More recently, EP No. 0218998 discloses a process to recover elemental iodine from aqueous sodium iodide by acidification with carbon dioxide and oxidation with molecular oxygen. These processes do not provide for the recovery of elemental iodine from organic iodides. U.S. Pat. No. 4,085,200 discloses a process for the thermochemical generation of methane and oxygen from water and carbon dioxide which utilizes as an intermediate step the hydrolysis of iodomethane to methanol, dimethyl ether, and aqueous HI; however, this process does not allow the product of elemental iodine or of an alkanol. U.S. Ser. No. 082,300 discloses a process for recovery of the iodine values from iodoalkanes by catalytic combustion; however, this process converts the organic moiety into worthless carbon dioxide and water. There thus exists a need for a Process which can economically recover the iodine values from an iodoalkane which also allows recovery of the organic moiety as an alkanol or dialkyl ether.

Simple hydrolysis of iodoalkanes by water in principle will yield alkanol and aqueous hydriodic acid; however, this does not allow a commercially feasible process because the reaction equilibrium

lies far to the left, limiting the conversion to a few percent. Moreover, recovery of concentrated HI from the dilute aqueous medium is expensive.

We have now found that the iodine values in iodoalkanes can be readily recovered in an economic fashion by carrying out a liquid phase oxidative hydrolysis whereby hydrolysis of the iodoalkane is carried out in the Presence of molecular oxygen and water at temperatures above about 100° C. Under these conditions, the HI liberated by hydrolysis is rapidly oxidized to elemental iodine. The net reaction is therefore

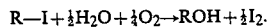

The iodine formed in this process is relatively insoluble in the aqueous medium and can be readily recovered by a variety of processes, including decantation where the iodine is molten, filtration when the iodine is solidified by cooling, or by extraction with a hydrocarbon solvent. The alkanol values can also be removed from the aqueous solution by distillation for low boiling alkanols, such as methanol or ethanol or by extraction for higher boiling, less hydrophilic alkanols.

The iodoalkanes which can be employed by this process contain from one to about 20 carbon atoms, and include primary, secondary, and tertiary iodoalkanes, and may contain optionally, besides hydrogen, heteroatoms such as sulfur and oxygen. Preferably, the iodoalkane is a secondary or primary iodoalkane with one to 5 carbon atoms. Suitable iodoalkanes include iodomethane, iodoethane, 1-iodopropane, 2-iodopropane, 1-iodobutane and 2-iodobutane. Suitable hydroxy-substituted alkanes include iodoethanol, iodopropanol, 1-iodo-4-butanol and 2-iodo-3-butanol. Suitable oxygen-substituted aklanes include 1-iodo-2-methoxypropane. Suitable sulfur-substituted alkanes include iodoethanethiol and iodoethyl methyl sulfide. More preferably is a primary iodoalkane with one to three carbon atoms, such as iodomethane, iodoethane, and idoethanol. The most preferred iodoalkane is iodomethane.

The reaction will occur at temperatures from about 50° C. to about 250° C. At lower temperatures the reaction rate becomes unacceptably slow, while at the higher temperatures the reaction pressure becomes unacceptably high. Preferred temperatures are from about 100° C. to about 200° C.; more preferred temperatures are in the range from about 125° C. to about 175° C.

The molecular oxygen can be supplied to the reaction in any convenient form, including air, enriched air, pure oxygen, and depleted air.

The pressure of oxygen supplied can be varied from subatmospheric to superatmospheric, but superatmospheric pressures are preferred. Preferred total pressures range from about 15 psia to about 1,500 psia, with a more preferred range of 100 psia to 1,000 psia. The pressure of the reaction must be sufficient such that an aqueous phase is maintained in the reactor.

The reaction can be run either continuously or in a batch mode. For large scale operation a continuous mode is preferred, while for small operation a batch mode may be preferrable.

The reaction time is dependent on the reaction temperature and pressure, but is in general between 10 hours and 10 minutes. Higher temperatures and pressures favor shorter reaction times.

In the process of this invention no catalyst is required. This simplifies the process operation since catalyst removal equipment is not required and the additional expense of catalyst is not incurred.

EXAMPLES

The following examples illustrate the operation of the present invention. In each, the specified reactants were loaded into a 330 mL Hastelloy C autoclave and were subjected to the specified reaction conditions and times. The reaction product was then removed and submitted for analyses. All percentages are in weight %.

EXAMPLE 1

100 mL H$_2$O
10 mL iodomethane
120° C.
200 psig air
one hour

The reaction consumed all available oxygen. The reaction solution contained 81.8% H$_2$O, 3.85% methanol, and 12% iodine, and 0.0% iodomethane. In addition, several grams of crystalline iodine were found in the autoclave.

EXAMPLE 2

100 mL H$_2$O
10 mL iodomethane
150° C.
400 psig air
one hour

The reaction exhibited a 100 psi pressure drop over 30 minutes. The reaction solution contained 89.7% water, 3.71% methanol, 3.78% iodine, and 0.0% iodomethane. In addition 15 grams of crystalline iodine were found in the autoclave. This example exhibits the high reaction rate for the oxidative hydrolysis reaction at 150° C.

EXAMPLE 3

100 mL H$_2$O
10 mL iodomethane
100° C.
400 psig air
one hour

The reaction solution contained 95.1% water, 1.15% methanol, 1.1% iodine, and 0.7% iodomethane. In addition, liquid iodomethane was found as a second layer. No crystalline iodine was found. This example exhibits the lower reaction rate for the oxidative hydrolysis reaction at 100° C.

EXAMPLE 4

100 mL H$_2$O
10 mL iodoethane
120° C.
400 psig air
two hours

The reaction Pressure dropped 94 psi over a period of one hour. The reaction solution contained 12.3% ethanol, 4.5% diethyl ether, 5.3% iodine, and 76.1% H$_2$O. In addition, 10.1 grams of crystalline iodine were found in the autoclave.

EXAMPLE 5

100 mL H$_2$O
10 mL 2-iodopropane
120° C.
400 Psi air
two hours

The reaction pressure dropped 75 psi over a period of one hour. The reaction solution contained 13.2% 2-propanol, 6.2% iodine, and 78.3% water. In addition, 3.4 grams of crystalline iodine were found in the autoclave.

We claim:
1. A process comprising
   A. preparation of an alkanol and elemental iodine by contacting an iodoalkane, an oxygen-substituted iodoalkane, a hydroxy-substituted iodoalkane or a sulfur-substituted iodoalkane containing 1 to 20 carbons, water and molecular oxygen at a temperature in the range of about 50° to about 200° C., and
   B. recovering the elemental iodine.
2. The process of claim 1 wherein the iodoalkane compounds contains 1 to 5 carbons.
3. The process of claim 1 wherein the temperature is in the range of about 100° to 200° C.
4. A process comprising
   A. preparation of methanol and elemental iodine by contacting iodomethane, water and molecular oxygen at a temperature in the range of 125° to 175° C., and
   B. recovering the elemental iodine.

* * * * *